US010335340B2

(12) United States Patent
Prince (10) Patent No.: US 10,335,340 B2
(45) Date of Patent: Jul. 2, 2019

(54) MOBILE DENTAL INTELLIGENCE CENTER

(71) Applicant: KevinTyrone Prince, Upper Marlboro, MD (US)

(72) Inventor: KevinTyrone Prince, Upper Marlboro, MD (US)

(73) Assignee: Dr. Kevin T. Prince, Honolulu, HI (US)

( * ) Notice: Subject to any disclaimer, the term of this patent is extended or adjusted under 35 U.S.C. 154(b) by 353 days.

(21) Appl. No.: 14/977,258

(22) Filed: Dec. 21, 2015

(65) Prior Publication Data

US 2017/0000677 A1    Jan. 5, 2017

Related U.S. Application Data

(60) Provisional application No. 62/188,075, filed on Jul. 2, 2015.

(51) Int. Cl.
| A61G 15/16 | (2006.01) |
| A61C 17/06 | (2006.01) |
| A61C 1/00 | (2006.01) |
| A61C 17/02 | (2006.01) |
| A61G 12/00 | (2006.01) |
| A61B 1/24 | (2006.01) |
| A61B 1/04 | (2006.01) |
| A61B 5/01 | (2006.01) |
| A61B 5/0205 | (2006.01) |

(52) U.S. Cl.
CPC ............ *A61G 15/16* (2013.01); *A61C 1/0015* (2013.01); *A61C 17/0217* (2013.01); *A61C 17/046* (2013.01); *A61G 12/008* (2013.01); *A61B 1/04* (2013.01); *A61B 1/24* (2013.01); *A61B 5/01* (2013.01); *A61B 5/02055* (2013.01); *A61B 2560/0437* (2013.01); *A61B 2562/227* (2013.01)

(58) Field of Classification Search
CPC ....... A61G 15/14; A61G 15/16; A61C 1/0053
See application file for complete search history.

(56) References Cited

U.S. PATENT DOCUMENTS

| 3,081,542 A * | 3/1963 | Sherfey .................. A61G 15/14 433/101 |
| 3,636,633 A * | 1/1972 | Fuller .................... A61G 15/14 433/108 |
| 3,777,746 A * | 12/1973 | Kwok .................. A61C 17/028 128/DIG. 10 |

(Continued)

*Primary Examiner* — Sarah B McPartlin (57) ABSTRACT

The Mobile Dental Intelligence Center (MobiDIC) will roll up alongside the patient's Bedside or Chairside where Oral Hygiene can be performed by the patient's Caregiver, with no need to have a sink or basin in the area. Using the MobiDIC the Caregiver will be able to brush the patient's teeth, rinse and suction the patient's mouth at the Bedside or Chairside; also the Caregiver will monitor the patients Vital Signs. The unit's unique cylindrical design makes it easy for the Caregiver to wipe clean and disinfect the unit. The air, water, suction and power supply hoses are internal to the unit reducing cord entanglement and trip hazards. The MobiDIC allows the Caregiver the ability to easily connect various medical monitoring devices including Intra and Extra Oral Cameras capturing images of the patient's mouth inside and the patient's general appearance. All MobiDIC innovations will facilitate assessing the patient's current general health.

4 Claims, 12 Drawing Sheets

(56) References Cited

U.S. PATENT DOCUMENTS

| | | | | |
|---|---|---|---|---|
| 5,013,240 A | * | 5/1991 | Bailey | A61C 1/0053 |
| | | | | 433/77 |
| 5,211,558 A | * | 5/1993 | Bailey | A61C 1/0053 |
| | | | | 433/77 |
| 5,655,905 A | * | 8/1997 | Jaimes | A61C 17/043 |
| | | | | 312/209 |
| 6,217,328 B1 | * | 4/2001 | Oliver | A61C 1/0084 |
| | | | | 433/29 |
| 7,490,837 B2 | * | 2/2009 | Pond | A61B 17/00 |
| | | | | 280/47.35 |
| 9,474,848 B2 | * | 10/2016 | Williams | A61M 3/0229 |
| 9,681,932 B2 | * | 6/2017 | Chun | A61C 17/043 |
| 2017/0065355 A1 | * | 3/2017 | Ross | A61B 34/30 |

\* cited by examiner

MOBILE DENTAL INTELLIGENCE CENTER

FIELD OF INVENTION

The invention relates generally to a portable dental unit that can provide the majority of basic tools and instruments necessary for oral hygiene maintenance and vital sign monitoring. The objective of the present invention is to provide caregivers of disabled, bedridden and incapacitated patients with the ability to conveniently provide adequate and timely oral hygiene to the patient. Additionally, the invention will provide caregivers the ability to monitor and report on the patient's vital signs. The present invention may be utilized for a daily regimen of oral hygiene and to check the vital signs of the patients through care delivered by the caregiver.

BACKGROUND OF THE INVENTION

Present day, the global population is aging and people are living longer lives due to rapid advances in medicine, which now grants physicians the means to prolong life by providing effective treatment for what were once fatal diseases. The internet has helped to make the world's population become smarter, in regards to taking care of one's overall health and finding ways to improve health outcomes through preventive medicine.

Although the population worldwide is aging and living longer, many in our population suffer from incapacitating illnesses that leave them partially or completely disabled. Hence, the rapid increase in home healthcare, assisted living facilities, nursing homes, and rehabilitation facilities etc.

Many in the country's aging population are receiving the basic nursing care they require on a daily basis in these types of settings. Such care includes: feeding, cleaning, medication delivery, transportation, and basic personal hygiene, which, more often than not, do not include basic dental/oral hygiene care. Caretakers often forget about or neglect Oral Health when they are tending to the overall health of the person they are delivering care to. This is not the caretaker's fault; it is a result of the under-emphasis on good oral health and its relationship to overall health in our society. Most medical school students receive little if any training on the oral cavity and the relationship of the mouth to the rest of the human body. The oral cavity/mouth is a major organ of the human body, and is the only portal or gateway food, good nutrition, and hence good health.

Many in the medical and dental communities are starting to realize the importance of good oral/dental health in the total health of the human body. Many medical schools are starting to expand their curriculums providing students with a more robust knowledge of oral/dental health and its relationship to the total health of the humans' species.

More and more in-depth research is underway, and finding important links between conditions common to the mouth and their relationship to systemic conditions in the rest of the body. The relationship between diabetes, a systemic condition and periodontal disease in the mouth has been established through copious research and published peer-reviewed articles.

It is an objective of the present invention to put the appropriate emphasis on good oral/dental health as an integral component of good overall health. The present invention will provide caregivers of disabled, bedridden and incapacitated patients a portable instrumentation platform with the ability to conveniently provide adequate and timely oral/dental hygiene to the patient on a regular basis along with vital sign monitoring.

The invention may be marketed at organizations and entities such as: Nursing Homes, Assisted Living Facilities, Mentally & Physically Disabled Patients who require caregivers in-home, Remote Military Medical facilities and other Locations, Hospitals (Public/Private/VA with incapacitated/critical patients, Dental Assisting/Medical Assisting Trade Schools, Nursing Schools, Inpatient Rehabilitation Centers, and Mental Health Facilities with Disabled Patients.

SUMMARY OF THE INVENTION

The present invention is a portable instrumentation platform equipped with a variety of dental tools and related equipment, designed to allow a caregiver the ability to provide oral hygiene maintenance. The caregiver will be able to monitor the patient's vital signs and if necessary, provide timely information to the patient's physician or dentist. The caregiver can utilize the intraoral/extraoral camera to take pictures inside and outside of the patient's mouth, and relay that information to the healthcare professional electronically via a secure network.

The present invention is designed to be easily cleaned and disinfected. It is also designed for simplicity, it is meant to make it easy for the caregiver to provide oral hygiene care at the patient's chairside or bedside.

The caregiver using the present invention, with appropriate training, should be able to brush the patient's teeth, rinse the patient's mouth, and deliver a mouthwash rinse right at the patient's bedside/chairside. Additionally, the caregiver will have all the tools necessary to accurately monitor the patient's vital signs.

This device is design to improve the oral health and monitor the overall health of the patient. The goal would be to enhance the caregiver's ability to attend to the overall health and welfare of the patient, which includes providing daily oral hygiene maintenance.

DETAIL DESCRIPTIONS OF THE INVENTION

All illustrations of the drawings are for the purpose of describing selected versions of the present invention and are not intended to limit the scope of the present invention.

Figure 5:
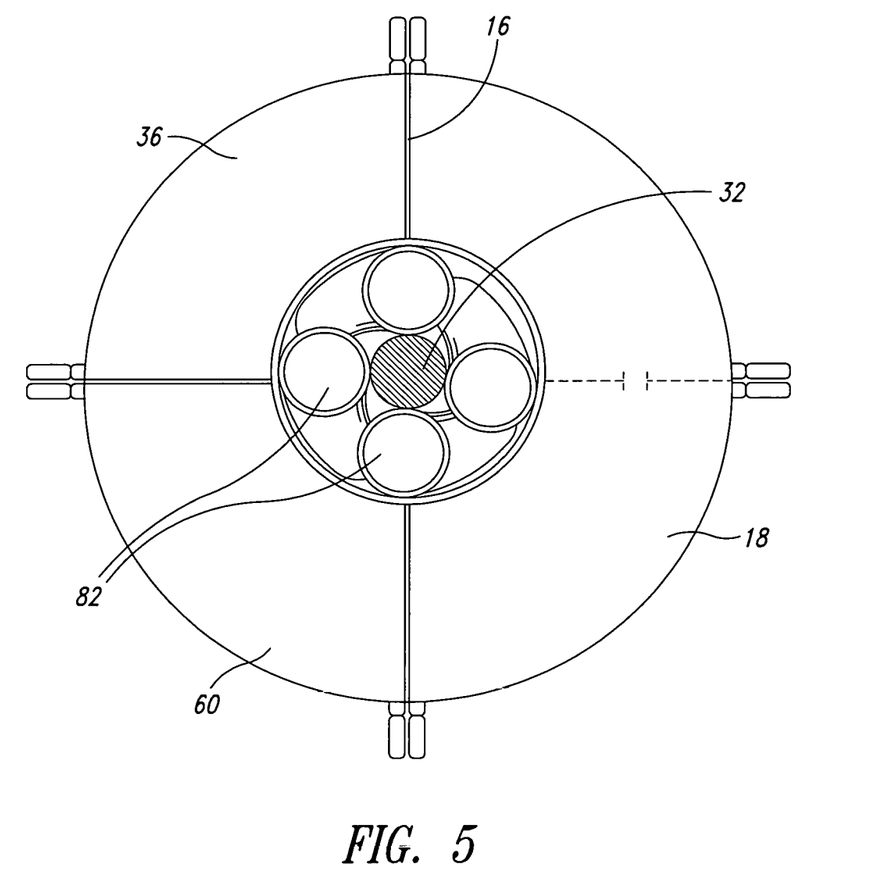
FIG. 5 depicts an exploded, interior mechanical view of the present invention.
Figure 6:
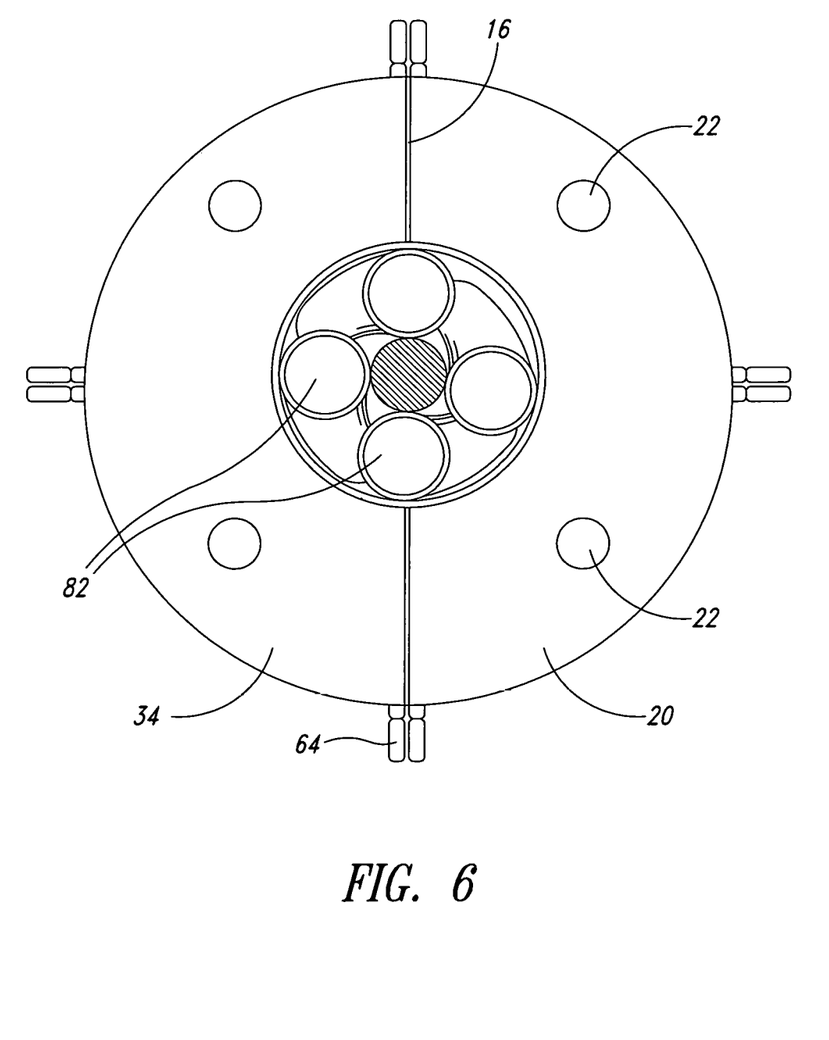
FIG. 6 depicts the reservoir view of the present invention.

In the present invention, a mobile dental apparatus/unit comprising of: a cylindrically arranged housing, a center support beam and distribution center (32) for wiring and supply/lines hoses, as viewed in FIGS. 5 and 6, a set of compartment featuring, a set of supply hoses, an optional intraoral/extraoral camera, a lightweight materials composition and arrangement process, a set of solar panels (2), a fold down handle (54), a digital clock/room temperature display (44), a mouthwash reservoir (12), a toothbrush rinse (14), a motherboard/computer nerve center (38), a supply platform (40), an air compressor (36), a suction pump (18), a waste water reservoir (20), a clean water reservoir (34), a set of reservoir drains (22), a clean water reservoir level indicator (6), a waste water reservoir level indicator (8), a water pump (60), a height adjustor (24), a rechargeable means of electrical power supply (26), a main power supply indicator (4), a set of USB/data port attachments (58), a set of supply hose/line attachments (56), a set of USB ports (58), a blood pressure and pulse indicator (46), a toothbrush timer (42), an On/Off/Pause indicator (52), a reset button (50), a digital display (74), a retractable power cord wall plug (66), a variable speed electric toothbrush, a set of 360 degree rotating and extendable wheels (64), a digital display (74) and a digital display swivel (76), a set of biofilm contamination sensors, a set of data connection capabilities, a remote control, an optional robotic arm for beverage dispensing and instrument manipulation, and a plurality of peripheral items, to include but not limited to an attachable computer monitor.

Notably, some of these components/processes may themselves be comprised of other subcomponents/sub-processes, which will be described in detail later in this disclosure.

The first major component/process of the present invention is the cylindrically arranged housing. Notably, the housing is not in the form of a rectangular prism, which is common for most dental units. The cylindrical arrangement makes the present invention more portable, as well as easier to clean and disinfect. The streamlined ergonomic design renders the unit easy to manipulate and handle for the caregiver. Supply lines/hoses and instrumentation are self-contained inside the cylindrical housing, described in the next section.

The next major component/process of the present invention is the center support pole and distribution center for wiring and supply lines/hoses. Unlike the majority of dental units, the supply hoses are housed in a central column. The hoses are neither exposed nor dangling. This mitigates the chances of entanglement with nearby objects, which is common with conventional dental units.

The next major component/process of the present invention is the set of compartment features. This set is comprised of compartment dividers (16), ventilation holes (72), compartment latches (10), and storage compartment doors (30). as viewed in FIGS. 2 and 7.

The compartment dividers (16) are interior walls, which divide sections of the present invention's interior. The compartments formed act as extra storage space for attachable equipment, such as the camera, blood-pressure cuff, thermometer, pulse oximeter, etc.

There are ventilation holes (72) as part of the compartment features. These are used for air exchange to the various compartments.

Each compartment has a latch. This is a closure for the individual compartments.

The last feature of the compartments is the set of storage compartment doors providing a plurality of access openings.

The next major component/process of the present invention is the set of supply lines/hoses. These are industry-standard retractable service cords, which provide air and/or water syringe capabilities and also support the toothbrush, suction and other mechanical parts.

The next major component/process of the present invention is the optional intraoral/extraoral camera. The user can utilize the camera to take pictures inside and outside the patient's mouth. The user can relay that information to the healthcare professional electronically via a secure network.

The next major component/process of the present invention is the lightweight materials composition and arrangement process. While materials composition normally does not factor into patentability, it matters here due to the needs of the invention.

Notably, there may be arrangement features, with an industry-standard lightweight, load-bearing efficient framework. The materials composition will be structurally sound but lightweight. The present invention as a whole should be easily portable via the rotating wheels, and the caregiver, without difficulty, can manipulate the present invention.

The next major component/process of the present invention is the set of solar panels (2). The user has the option to recharge the main power source using solar energy. In the invention's preferred embodiment, the solar recharge panels (2) are located adjacent to the handle, on the present invention's exterior. These are depicted in FIGS. 1-4. These solar panels (2) can be used to recharge the main power source if sufficient sunlight is available.

The next major component/process of the present invention is the fold down handle (54). This is an industry-standard fold down handle (54) with the ability to flip either up or down depending on usage. It comprises of a handle bar with hinges or axles on both sides.

The next major component/process of the present invention is the digital clock/room temperature display (44). This is a combination digital clock and room temperature indicator. This functions as a dual-display in the invention's preferred embodiment. Alternative or future embodiments may utilize more displays or attributes, depending on the evolving needs of the industry.

The next major component/process of the present invention is the mouthwash reservoir (12). This is a container for storing mouthwash. It must be able to store the liquid with minimal evaporation of alcohol, to preserve the properties of the mouthwash fluid itself. The mouthwash can be dispensed via supply/lines and connectors for use.

The next major component/process of the present invention is the toothbrush rinse (14). This is a small component which projects a stream of water, used for cleaning out debris from the electric toothbrushes. Fluid from this small component will drain via supply lines/hoses to the waste water reservoir (20).

The next major component/process of the present invention is the motherboard/computer nerve center (38). This is the area of the invention that houses the CPU or CPUs. This computer nerve center in the invention's preferred embodiment will have a motherboard (38) with its own compartment. The motherboard (38) will be configured to handle the computer-related demands of this present invention as per standard computer engineering functionality. This can be seen in FIGS. 1-4.

The next major component/process of the present invention is the unit supply platform (40). The unit supply platform (40) functions as a central hub or nerve center for the present invention. This is the place where the bulk of the connections to this unit will take place. All supply hose connections (56) and USB data port connections (58) will be made through this supply platform (40). These connections are discussed later in this disclosure.

Figure 1:
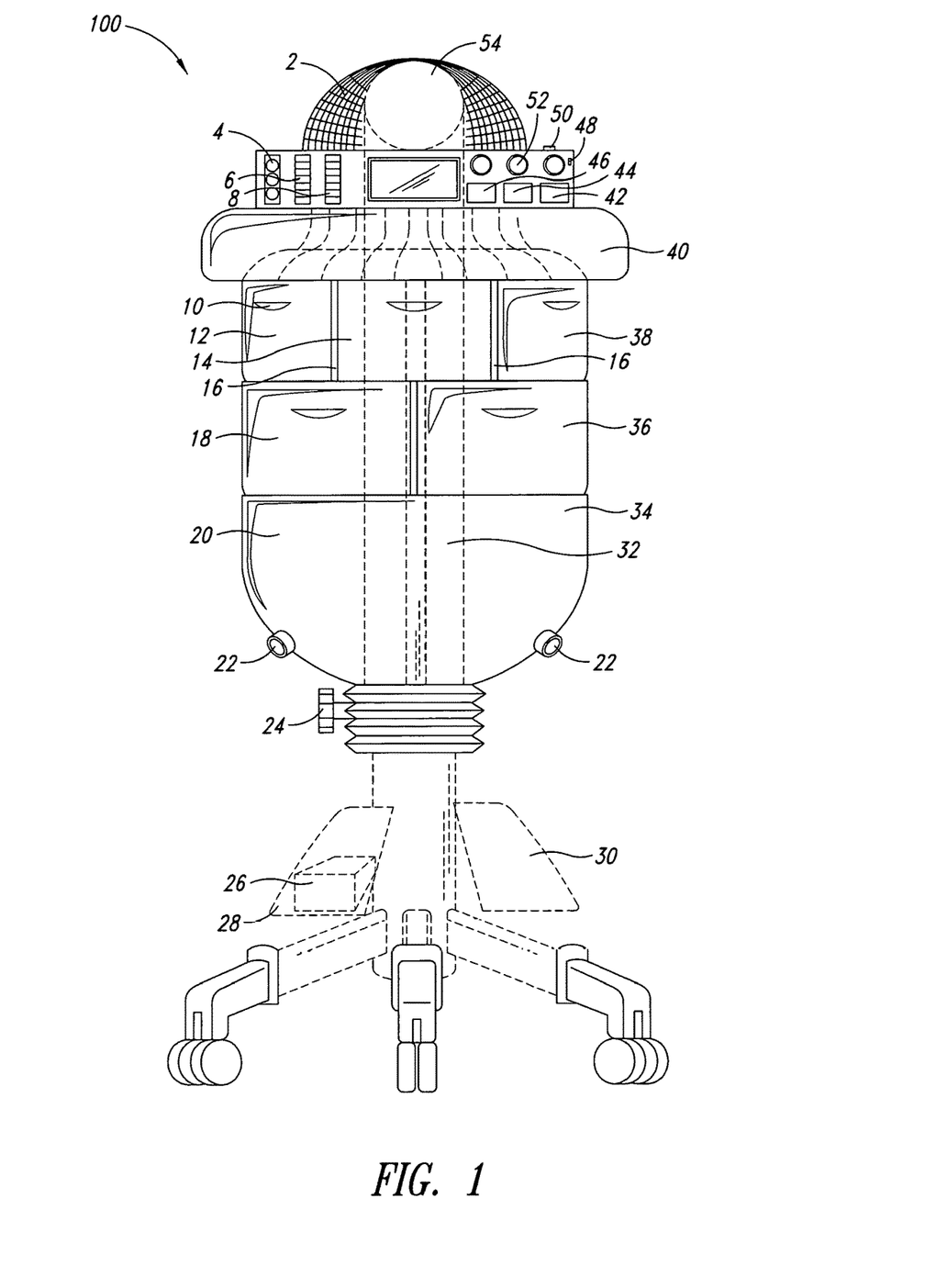
FIG. 1 depicts the front view of the present invention.

The next major component/process of the present invention is the air compressor, as viewed in FIG. 1. The air compressor's function is to push air up and out of the present invention to the extendable supply line/hose. Transport of both air and water will occur through the same supply line/hose and attach to the air/water syringe. This will produce an air/water spray, which is used to thoroughly rinse the patient's mouth.

The next major component/process of the present invention is the suction pump (18). The suction pump (18) will provide the suction pressure necessary to remove water and small particles of debris from the patient's mouth after rinsing. The suction pump (18) will be attached to an extendable supply hose that will rest on the supply platform (40), and may connect to a disposable suction tip, which can easily be inserted and removed for disposal.

The next major component/process of the present invention is the waste water reservoir (20). Notably, this is detachable. This reservoir (20) can also be drained without removing it from its emplacement. The reservoirs (20) will have the ability to tilt out for ease of filling and flushing. The drain plug at the base of the reservoir should be connectable to a drain hose for ease of drainage. In the invention's preferred embodiment, the reservoir (20) is a transparent or translucent container, with volume measures visible from the outside looking in.

The next major component/process of the present invention is the clean water reservoir (34). Notably, this is also detachable. This can also be drained without removing it from its emplacement. Notably, this reservoir supports the use of distilled water but potable water is also acceptable. In the invention's preferred embodiment, this reservoir (34) is also a transparent or translucent container, with volume measures visible from the outside looking in.

The next major component/process of the present invention is the set of reservoir drains (22). In the invention's preferred embodiment, there are two reservoir drain (22). These are for the clean water reservoir (34) and waste water reservoir (20), respectively.

Figure 10:
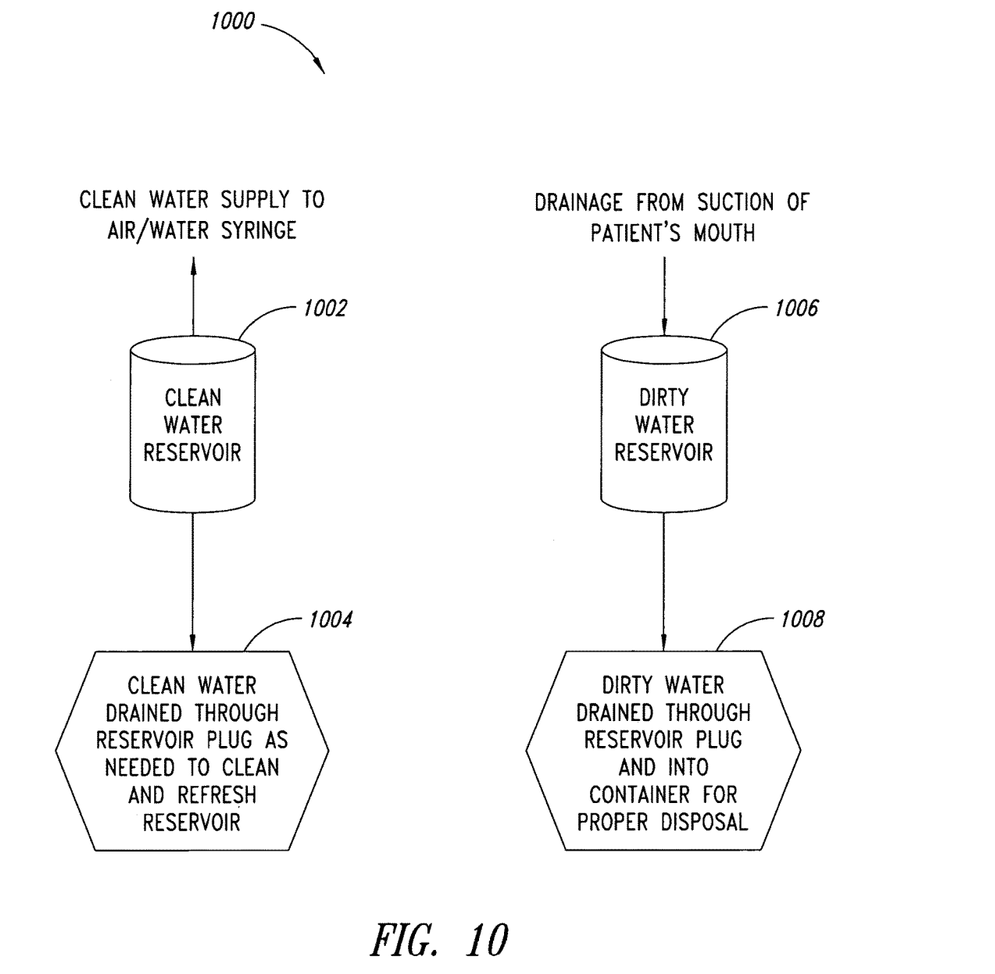
FIG. 10 is a flowchart depicting the water flow in relation to the reservoirs.

As mentioned, the reservoirs (20, 34) should have the ability to tilt out for ease of filling and flushing. The drain plug at the base of the reservoir should be connectable to a drain hose for ease of draining the reservoir. In this process; the upper reservoir drains into the waste water reservoir as viewed in FIG. 10.

In the invention's preferred embodiment, there is a female-to-male attachment for ease of draining into the waste water reservoir container, which will be used for emptying and disposal of fluid.

The next major component/process of the present invention is the clean water reservoir level indicator (6). This was mentioned earlier as being integrated into the reservoir as simple volume measures. In the invention's preferred embodiment this may be a simple series of measuring lines, on a transparent gauge. In alternative or future embodiments of the invention, this may be electronic or use a mechanical measuring method.

The next major component/process of the present invention is the waste water reservoir level indicator (8). This was mentioned earlier as being integrated into the reservoir as simple volume measures. This is nearly identical to the clean water reservoir level indicator (6) except it is used for the waste water. The key possible difference is that in electrical or mechanical embodiments of the invention, this indicator may include filters or sheaths to prevent contamination or accumulation of potentially clogging material.

The next major component/process of the present invention is the water pump (60). The function of this pump is to transfer water from the clean water reservoir (34) up and out the present invention's main body, and into the extendable supply line/hose, which will attach to an industry-standard air/water syringe.

The next major component/process of the present invention is the height adjustor (24). In the invention's preferred embodiment this is an industry-standard telescoping height system. In the invention's preferred embodiment, this height adjustor system is located at the bottom of the present invention. Alternative or future embodiments of the invention may utilize different means of height adjustment, such as a crank and screw or automatic.

The next major component/process of the present invention is the long life rechargeable main power source (26). In the invention's preferred embodiment, the rechargeable main power source (26) will be used to power all functions related to the present invention, while it is away from a wall outlet. The present invention can also be directly powered through connection to a wall outlet. If given enough sunlight, the set of solar panels (2) may be able to provide power as well this is depicted in FIGS. 2,3,7, and 9.

The next major component/process of the present invention is the main power source indicator (4). In the invention's preferred embodiment, the colors of the indicator may be red, yellow, or green. In alternative or future embodiments of the invention, the indicator may use a different display with finer granularity to more accurately depict the remaining power level. The indicator may utilize quantifiable numbers instead of colors in such embodiments.

Figure 2:
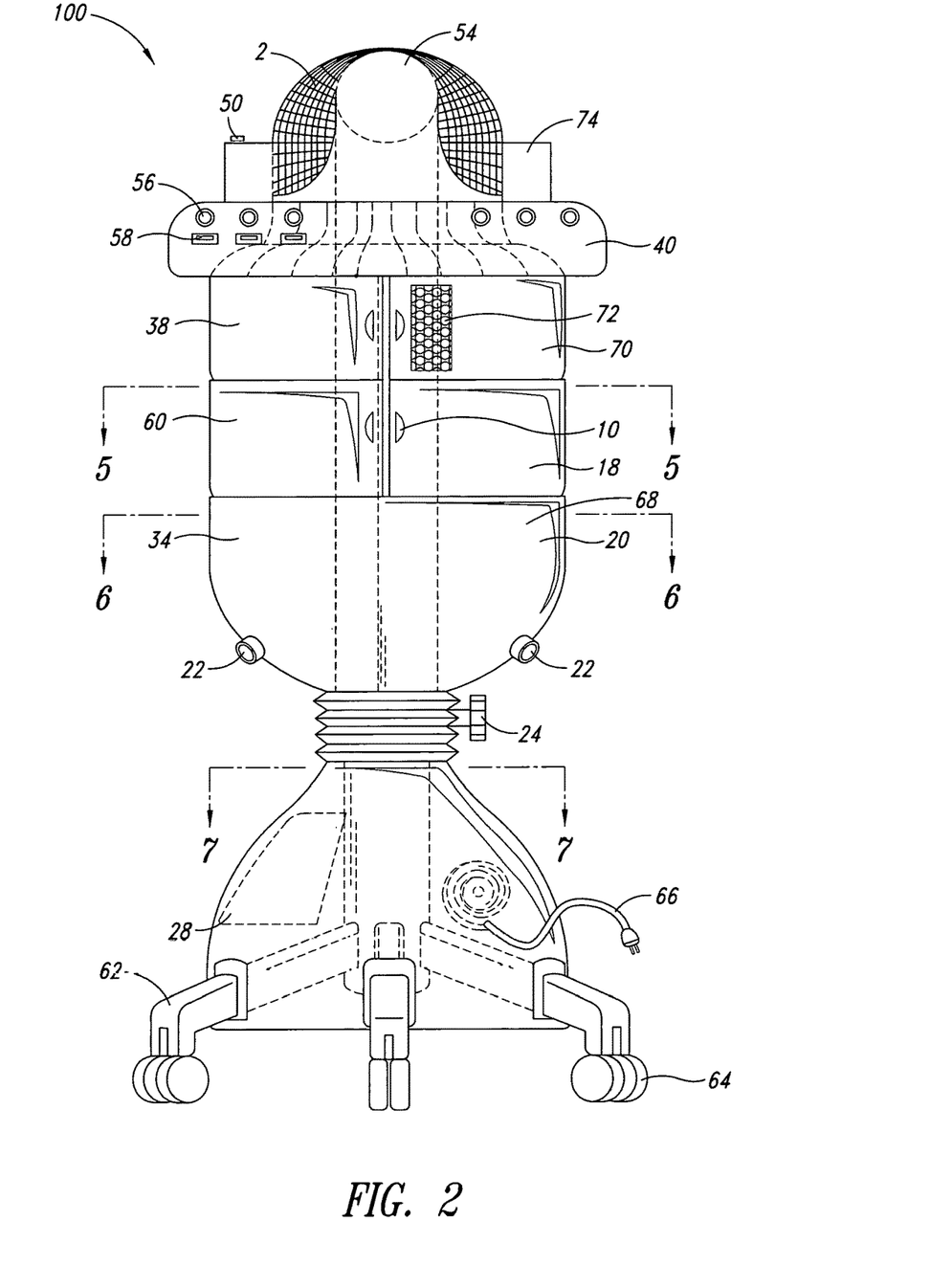
FIG. 2 depicts the back view of the present invention.
Figure 4:
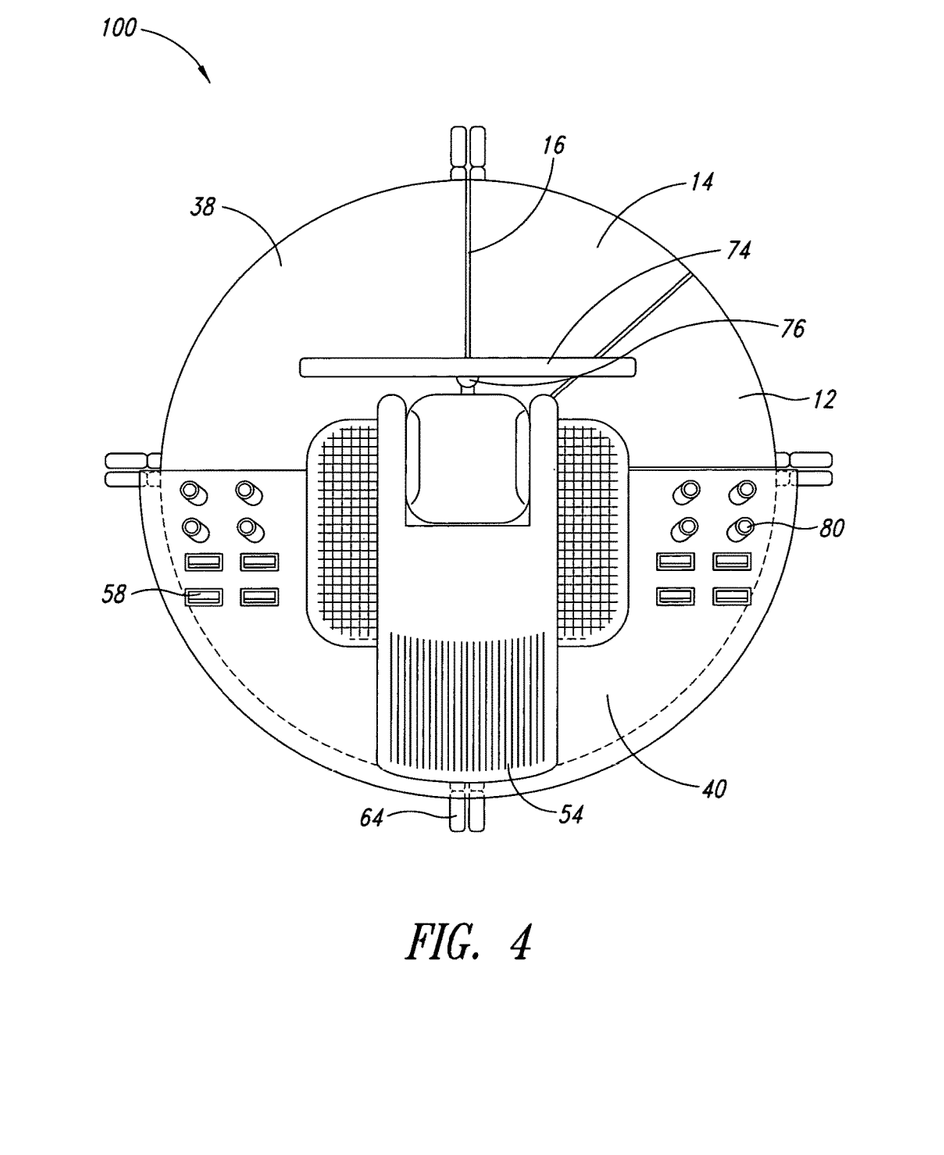
FIG. 4 depicts the top view of the present invention, through the handle and unit supply platform.

The next major component/process of the present invention is the set of USB/data port attachments (58) as viewed in FIGS. 2 & 4. These include but are not limited to: thermometer, blood pressure cuff, and pulse oximeter. In the invention's preferred embodiment these may be stored inside the interior compartments.

The next major component/process of the present invention is the main supply platform (40). This acts as a docking station for the caregiver's medical devices and a plurality of instruments.

The next major component/process of the present invention is the set of supply line/hose attachments. Notably, these are separate from the USB/data port attachments. They attach to one of the hoses connected to the supply platform. These attachments include but are not limited to electric toothbrushes.

The electric toothbrush that attaches to the unit will have variable speed. In the invention's preferred embodiment, the available speeds are high, medium, or low. Alternative or future embodiments of the invention may have finer granularity of control.

The next major component/process of the present invention is the set of USB ports (58) or other forms of data ports. As mentioned these ports are connection points for thermometers, blood pressure cuff, pulse oximeter, intraoral/extraoral camera, etc. There will be accompanying software to support the USB ports (58) and their connected devices, with possible custom firmware and drivers.

Notably, alternative or future embodiments of the invention may support other attached devices. One such device may be a portable glucose monitor of the finger-prick type with a display. Alternative or future embodiments of the invention may support a similar device for cholesterol testing.

The next major component/process of the present invention is the blood pressure and/or pulse indicator (46). This component warrants separate mention because of its importance in detecting a patient's blood pressure and heart rate.

The next major component/process of the present invention is the toothbrush timer (42). In the invention's preferred embodiment, this is a countdown clock for two minutes. At the conclusion of the duration the timer will sound an alarm. Alternative or future embodiments may utilize a different timed duration or time measuring device.

The next major component/process of the present invention is the On/Off/Pause indicator (52). These are industry-standard buttons for setting the state of the present invention. "On" will activate the present invention, "Off" will deactivate it, and "Pause" will halt processes but not turn off the machine.

The next major component/process of the present invention is the reset button (50). This will reboot the present apparatus/unit.

The next major component/process of the present invention is the back view digital display (74) This is an illuminated display, which will show all information regarding the patient's vital signs, such as blood pressure, temperature, etc. It will also display any information regarding the status of the unit, such as reservoir fluid levels, power status, and Wi-Fi/Internet connection status where applicable, etc.

Figure 3:
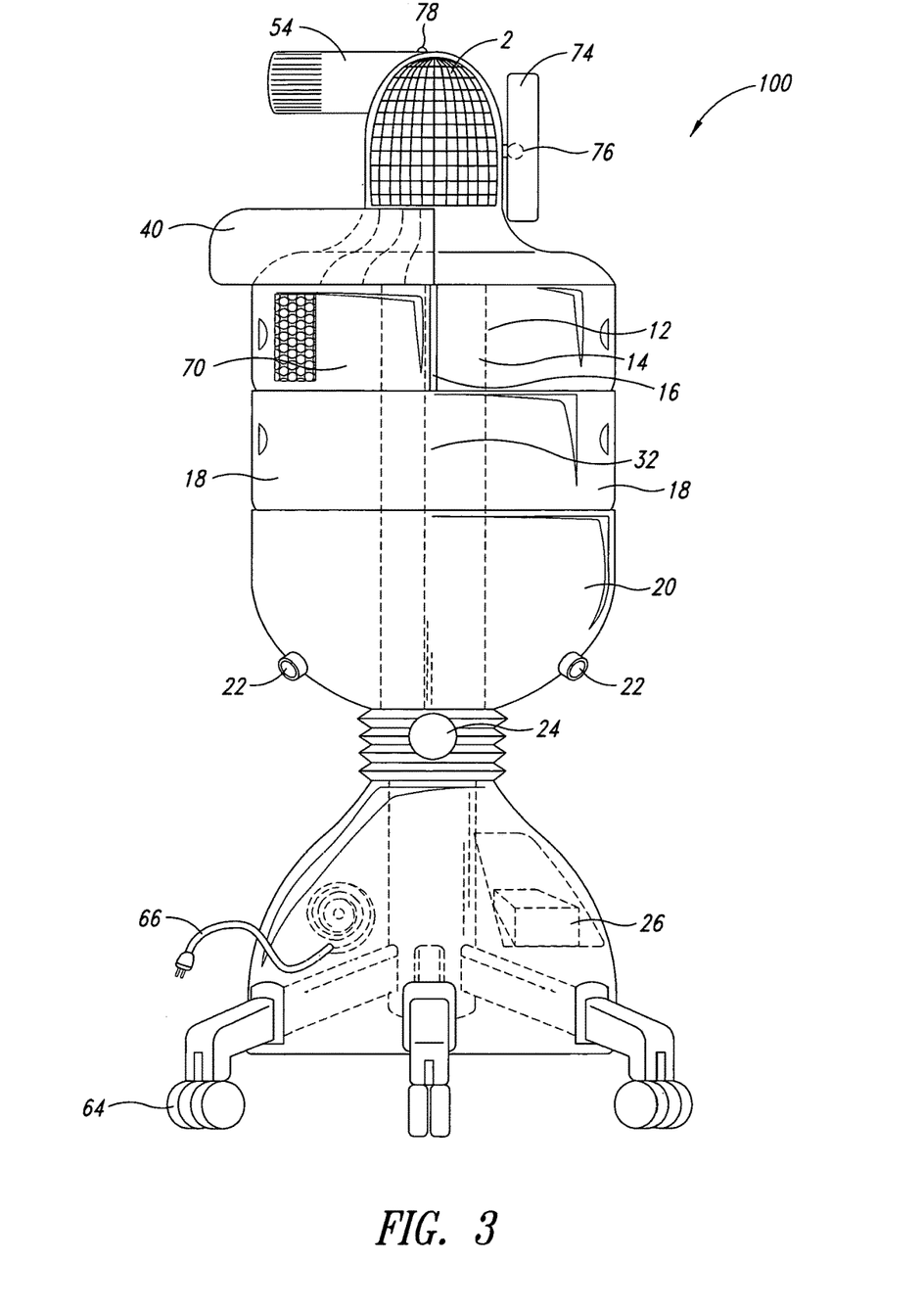
FIG. 3 depicts the side view of the present invention.
Figure 7:
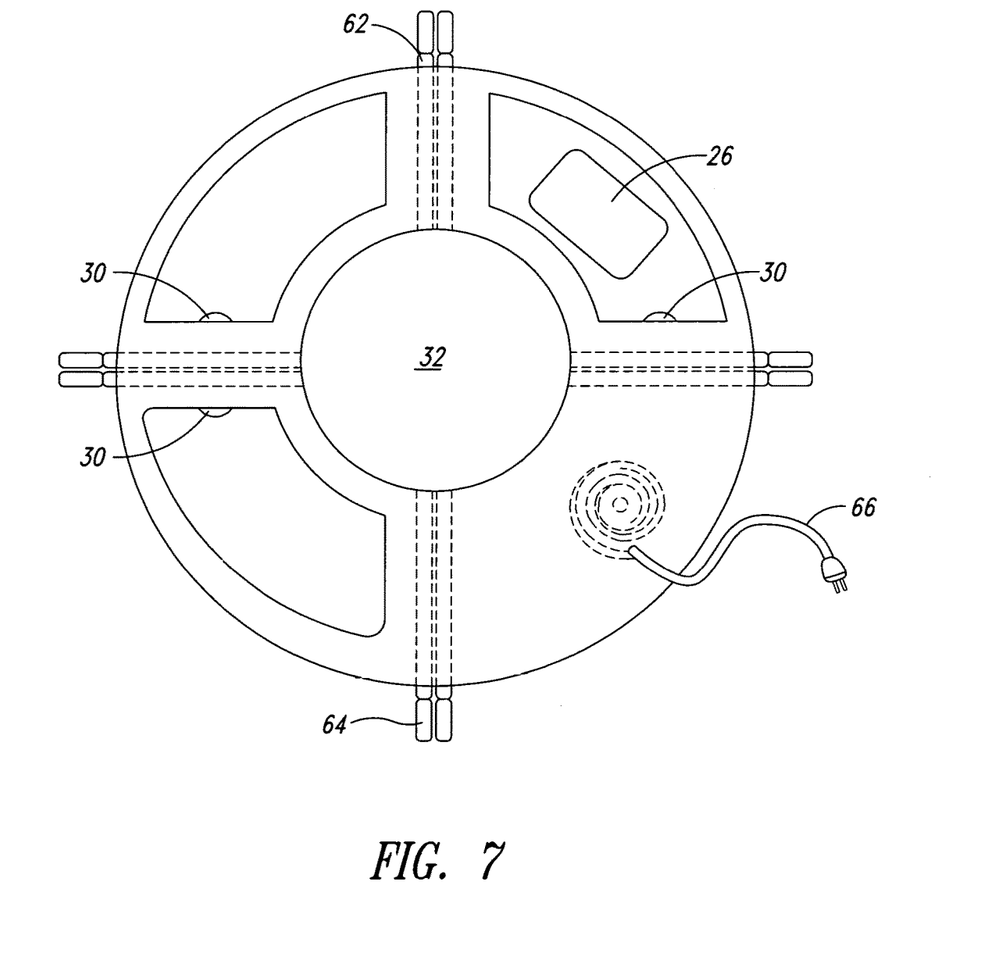
FIG. 7 depicts the lower base view of the present invention.
Figure 8:
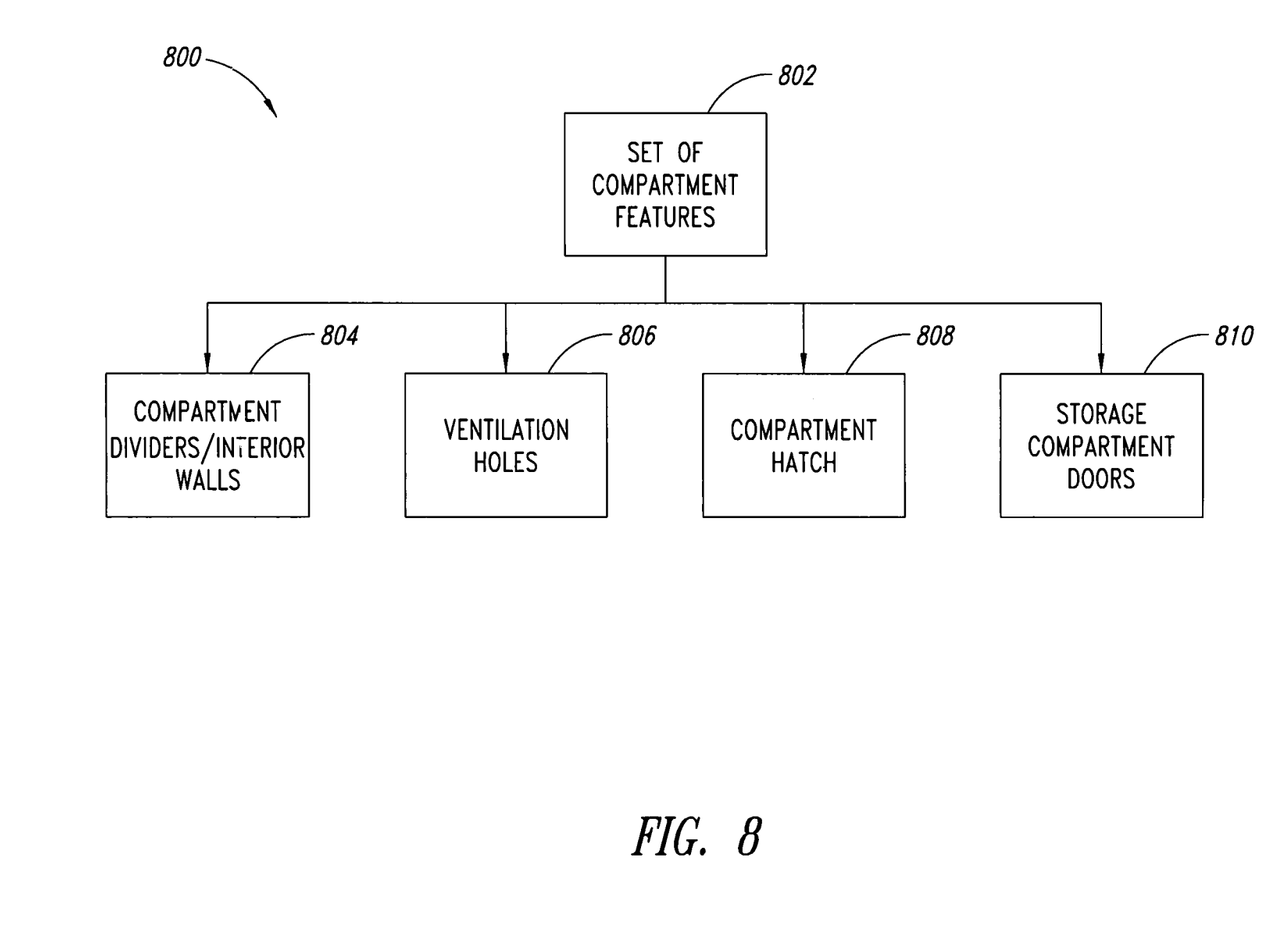
FIG. 8 is a flowchart depicting the constituent relationship of the compartment features.
Figure 9:
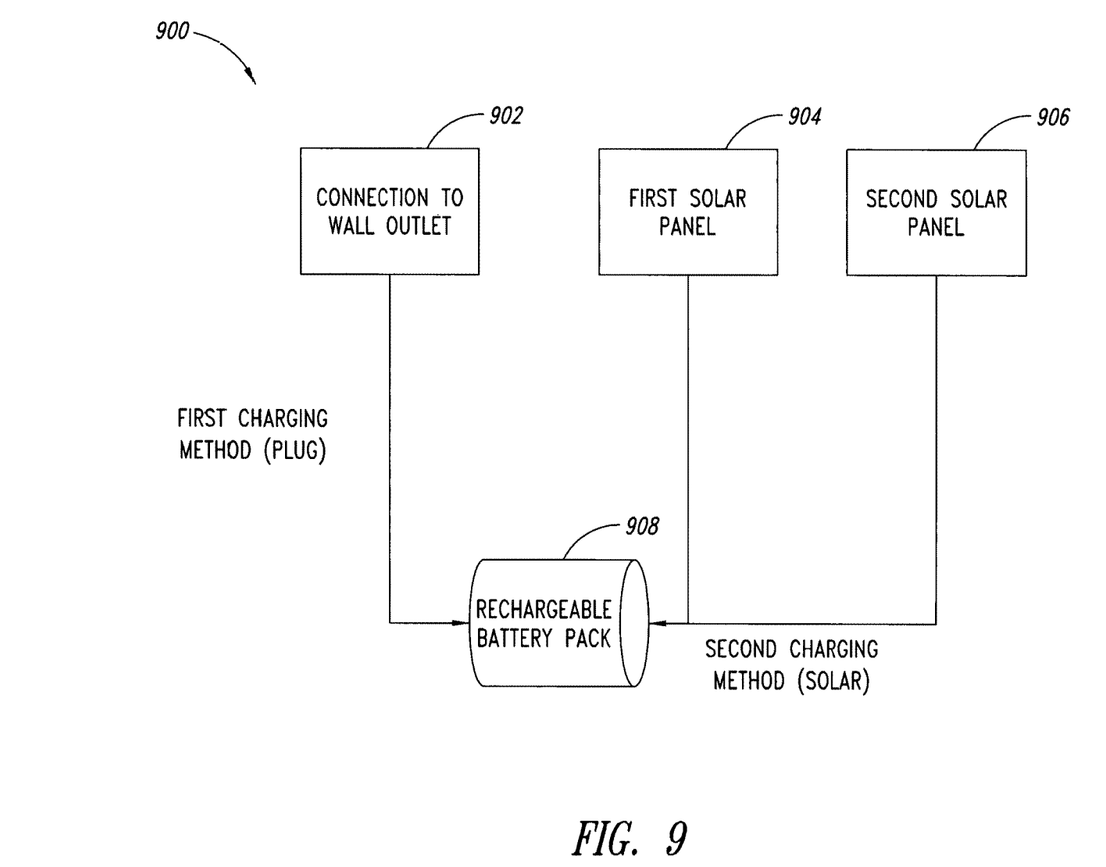
FIG. 9 is a flowchart depicting the possible methodologies for charging the battery, including the solar panels.

The next major component/process of the present invention is the retractable power cord wall plug (66), as viewed in FIGS. 2,3, and 7. In the invention's preferred embodiment this is an 8-12 foot retractable power cord. It will come standard with the unit, with the option for purchase of an extension power cord if additional length is required. Notably, there is built-in surge protection.

The next major component/process of the present invention is the set of extendable wheels (62) as viewed in FIGS. 2 and 7. In the invention's preferred embodiment the wheels have a 3" diameter. The wheels will have 360-degree rotation, and extend out to 4 inches from the base. The wheelbase will be wide to maximize stability, of the apparatus/unit. Alternative or future embodiments of the invention may utilize different dimensions depending on the evolving needs of the industry.

The next major component/process of the present invention is the digital display, as viewed in FIGS. 2, 3, and 4. This allows the digital display to rotate, up to 180 degrees. This allows both the user and the patient to view photo images and other digital readouts with ease.

The next major component/process of the present invention is the set of biofilm contamination sensors. These ensure biofilms have not contaminated the lines. This detection can be automated, and the set can comprise of internal sensors with notification components inside the hose.

If the sensor is disposable, it can possibly include a "change sensor" indicator for when the sensor becomes old.

The next major component/process of the present invention is the set of data connection capabilities. In the invention's preferred embodiment this comprises of both Internet capability as well as Bluetooth functionality.

In terms of Internet capability, the present invention can be Wi-Fi capable. It may support laptop connection and/or docking, and supports industry-standard Ethernet cords for network connection.

Bluetooth functionality will be used for the remote controller and streaming data feeds from the attached devices. Notably, all electronic connection via Wi-Fi meet industry-standard cybersecurity measures to preserve the confidentiality of Patient Health Information (PHI).

The remote controller is discussed later in this disclosure. The remote control may be utilized or viewed via a mobile device, such as a smartphone or tablet.

The next major component/process of the present invention is the remote control. This is a software process allowing the user to use the Bluetooth functionality as a connection means between a mobile device such as smartphone or tablet, and the present invention. The mobile device can thus act as a wireless remote control unit through relevant software processes. Data can be viewed and attachment tools may be controlled in this manner. Notably, alternative or future embodiment of the invention may include the support of infrared signals instead of Bluetooth. The infrared control may be standalone, or possibly a retrofit device for a mobile device.

Figure 12:
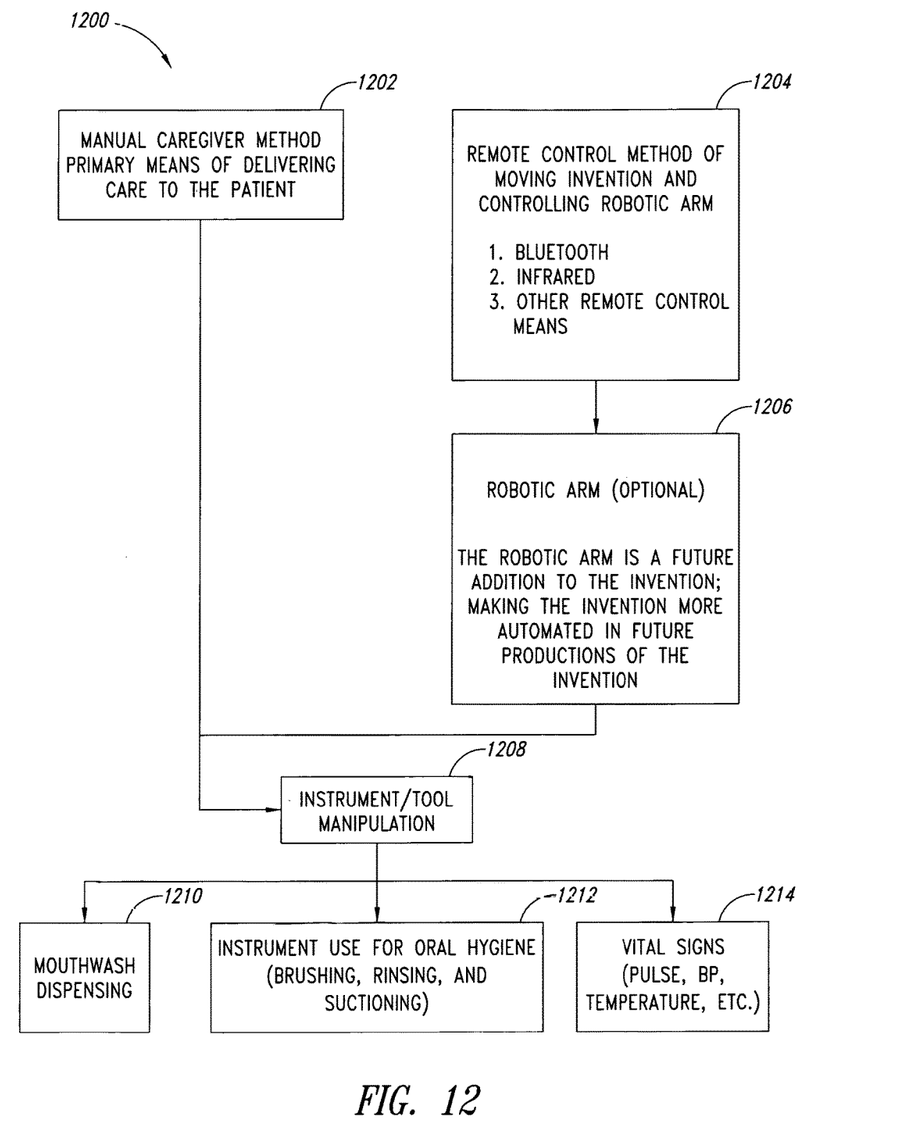
FIG. 12 is a flowchart depicting the sub-processes pertaining to the futuristic robotic arm.

The next major component/process of the present invention is the robotic arm for beverage dispensing and instrument manipulation. It may possess phalanges-type subcomponents. Notably, the arm may be used to perform teeth-brushing actions, vital signs monitoring and other service actions on the patient as depicted in FIGS. 12 (1204, 1206, 1208, 1210, 1212 and 1214).

It is important to note that the robotic arm is a complex subcomponent with its own constituent subcomponents and sub-processes, described as follows.

The arm will be able to grasp an electric toothbrush and deliver it to a patient's mouth for performing oral hygiene.

The hand of the robotic arm will be able to place the thermometer in the patient's mouth to obtain a temperature reading. The arms will also be able to place and remove the pulse oximeter on the patient's finger to read a patient's pulse.

The hand of the arm will be able to hold and manipulate the variable speed electric toothbrush in the patient's mouth, moving the electric toothbrush in a pre-programmed pattern based on the geography of the patient's mouth.

The intraoral/extraoral camera will take pictures of the inside and the outside of the patient's mouth and store images in the present invention's memory bank in the nerve center, to be retrieved and used by the arm to manipulate the electric toothbrush in specific motions based on the geography of the patients mouth.

The present invention will have built in indicators that can pinpoint problems within the system, to expedite maintenance and repairs as needed.

The electric toothbrush will have a slip-resistant grip to make it easier for the human hand and/or the robotic arm to grip.

The present invention will have the ability to shut itself down after a set period of non-use, this will conserve energy and protect against power surges.

The present invention can have optional voice activation much like the iPhone and its Siri personal assistant; this will allow the invention to communicate with a variety of external entities.

The present invention will have the option to carry out various tasks based on voice activation.

The present invention will be ergonomically designed to the greatest extent possible for ease of use.

The robotic hands on the arm will be able to pick up the intraoral camera, deliver it to the patient's mouth, and snap pictures based on remote manipulation by a user.

The robotic arms should have 360-degree rotation capabilities at all joints, namely the shoulder, elbow and hand.

The next major component/process of the present invention is the plurality of peripheral items. These are not directly related components of the present invention, but can be considered to be part of the present invention's overall delivery system. These may include marketing products and equipment, including but not limited to: a caregiver training video on recorded media, reservoir-cleaning solutions, disinfectant wipes, etc.

Herein follows a description of the usage of the present invention.

Figure 11:
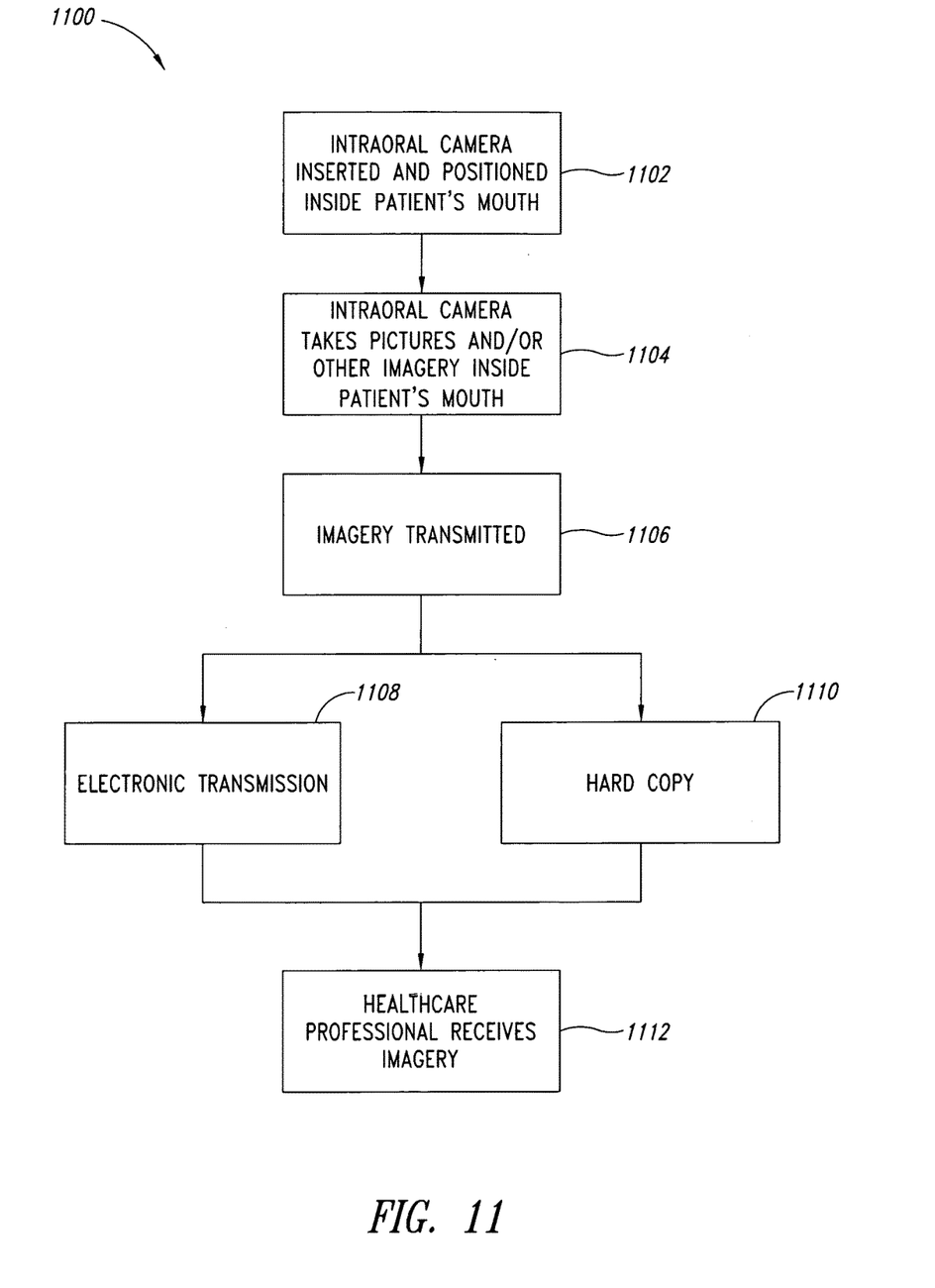
FIG. 11 is a flowchart depicting the intraoral/extraoral camera sub-processes.

The present invention is intended to roll up right alongside the patient bedside or chair so that the caregiver, with no need to have a sink or basin at the patient chair or bedside, can perform proper oral hygiene. While the present invention is alongside the patient, the caregiver can provide a host of vital sign assessments to gauge and report on the patients overall health condition i.e., blood pressure, temperature, pulse, oxygen saturation, blood sugar, cholesterol etc. An intraoral/extraoral camera can also be attached to the present invention, providing a picture and vital information about the condition of the patient's mouth and general appearance. This information can be provided to a dentist/physician for consultation and treatment as depicted in FIGS. 11 (1102, 1104, 1106, 1108, 1110, and 1112). The patient can view the pictures taken with the intraoral/extraoral camera using a monitor, which will help to facilitate the patient's education regarding their oral health and general health condition. A variety of external attachments can be connected directly into the present invention to monitor and assess the vital signs, oral health and general health of the patient.

One of the three fluid reservoirs attached to the unit will hold clean potable or distilled water to be used to rinse and clean the patients mouth after brushing, the other large reservoir will be used to store waste water suctioned from the patients mouth after brushing and rinsing has occurred. The third and smaller reservoir will have two separate compartments one compartment will hold mouthwash that can be dispensed for patient use, and suctioned back into the waste water reservoir. The other compartment will be used to rinse the patient toothbrush after use and prior to storage; the water in this reservoir is suctioned out into the larger waste water reservoir for proper disposal. The present invention will house several mechanical devices designed to move fluid, such as water and/or mouthwash, and air through the present invention.

Although the invention has been explained in relation to its preferred embodiment, it is to be understood that many other possible modifications and variations can be made without departing from the spirit and scope of the invention. Obvious changes, modifications, and substitutions may be made by those skilled in the art to achieve the same purpose the invention. The exemplary embodiments are not intended to limit the scope of the invention. It is intended that the present invention cover all other embodiments that are within the scope of the descriptions and their equivalents.

What is claimed is:

1. A portable dental and medical unit comprising:
   a wheelbase;
   a plurality of 360 degree rotatable wheels extending from the wheelbase and configured to movably support the unit on an underlying support surface;
   a central support beam extending upward from the wheelbase;
   a rechargeable power supply positioned within a power supply compartment and a retractable wall plug mounted on the central support beam adjacent said wheelbase;
   a cylindrical housing supported by the central support beam and spaced apart from the wheelbase, wherein the cylindrical housing is vertically adjustable with respect to the wheelbase by a unit height adjustor;
   the cylindrical housing has a bottom and a top and comprises series of elements including:
      a waste water reservoir with a reservoir drain positioned adjacent the bottom;
      a clean water reservoir with a reservoir drain position adjacent the bottom;
      a suction pump positioned adjacent said waste water reservoir or said clean water reservoir;
      an air compressor positioned adjacent said waste water reservoir or said clean water reservoir;
      a mouthwash reservoir positioned adjacent said suction pump;
      a toothbrush rinser positioned adjacent said mouth wash reservoir;
      a biofilm contamination sensor located near the waste water reservoir;
      a water pump;
      a unit control module; and
      a unit supply platform positioned within a unit supply storage compartment adjacent the mouth wash reservoir, toothbrush rinser and unit control module and near a top of the cylindrical housing, wherein the unit supply platform includes a series of inter-unit supply line attachment ports and a series of USB ports;
   a protrusion, including dual solar panels positioned on a surface thereof, extends upward from the top of the cylindrical housing and includes a foldable handle with slip-resistant grip mounted thereto and a 360 degree swivel digital display mounted thereto;
   wiring and inter-unit supply lines and hoses extend through the central support beam and are configured to attach to at least one of the series of elements, the rechargeable power supply or an electric toothbrush, a computer monitor or an air-water syringe and connector;
   wherein the 360 degree swivel digital display is configured to display information measured by one of said series of elements or an external health monitoring device including a digital blood pressure cuff, a digital thermometer, a digital pulse oximeter or a digital intra oral and extra oral camera connected to one of the series of USB ports.

2. The portable dental and medical unit of claim 1, further comprising a remote control configured to enable a caregiver using the unit to move the unit remotely and vertically adjust the cylindrical housing with respect to the wheel base.

3. The portable dental and medical unit of claim 1, wherein the rechargeable power supply is capable of being charged by electrical power provided through said retractable wall plug or by solar power collected by the dual solar panels.

4. The portable dental and medical unit of claim 1, wherein the unit control module is configured to wirelessly transmit information via Wi-Fi and/or Bluetooth and receive information transmitted electronically via remote technology or voice activation.

* * * * *